United States Patent
Kim et al.

(10) Patent No.: US 10,047,032 B2
(45) Date of Patent: *Aug. 14, 2018

(54) PREPARATION METHOD OF ORGANIC ZINC CATALYST AND POLY(ALKYLENE CARBONATE) RESIN

(71) Applicant: LG CHEM, LTD., Seoul (KR)

(72) Inventors: Sung Kyoung Kim, Daejeon (KR); Seong Kyun Kang, Daejeon (KR); Jun Wye Lee, Daejeon (KR); Seung Young Park, Daejeon (KR); Hyeon Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 68 days.

This patent is subject to a terminal disclaimer.

(21) Appl. No.: 14/734,856

(22) Filed: Jun. 9, 2015

(65) Prior Publication Data

US 2015/0361023 A1 Dec. 17, 2015

(30) Foreign Application Priority Data

Jun. 13, 2014 (KR) ........................ 10-2014-0072345
May 14, 2015 (KR) ........................ 10-2015-0067521

(51) Int. Cl.
  *C08G 64/34* (2006.01)
  *C07C 51/41* (2006.01)

(52) U.S. Cl.
  CPC ............ *C07C 51/418* (2013.01); *C08G 64/34* (2013.01)

(58) Field of Classification Search
  CPC .............................. C07C 51/418; C08G 64/34
  USPC .......................................... 528/414; 524/792
  See application file for complete search history.

(56) References Cited

U.S. PATENT DOCUMENTS 7,405,265 B2  7/2008  Moon et al.
2014/0155573 A1*  6/2014  Soler .......................... C08J 5/18
                                              528/405

FOREIGN PATENT DOCUMENTS

| CN | 102766039 A | * | 11/2012 |
| JP | 3000064 B2 | | 11/1999 |
| JP | 4708019 B2 | | 6/2011 |
| KR | 10-2014-0062130 A | | 5/2014 |

* cited by examiner

*Primary Examiner* — Kelechi Egwim
(74) *Attorney, Agent, or Firm* — Dentons US LLP

(57) ABSTRACT

The present invention relates to a preparation method of an organic zinc catalyst capable of preparing an organic zinc catalyst having a finer and more uniform particle size and more improved activity during a polymerization process for preparing a poly(alkylene carbonate) resin, and a preparation method of a poly(alkylene carbonate) resin using the organic zinc catalyst. The preparation method of an organic zinc catalyst includes reacting a zinc precursor and a dicarboxylic acid in the presence of a dispersant to form a zinc dicarboxylate-based catalyst, wherein a reaction step is performed under a condition at which the number of moles of the dicarboxylic acid present in a reaction system is larger than that of the zinc precursor throughout the entire reaction step.

13 Claims, No Drawings

PREPARATION METHOD OF ORGANIC ZINC CATALYST AND POLY(ALKYLENE CARBONATE) RESIN

CROSS REFERENCE TO RELATED APPLICATIONS

This application claims the benefit of Korean Patent Applications No. 10-2014-0072345 filed on Jun. 13, 2014 and No. 10-2015-0067521 filed on May 14, 2015 with the Korean Intellectual Property Office, the disclosures of which are incorporated herein by reference in their entirety.

FIELD OF THE INVENTION

The present invention relates to an organic zinc catalyst having a more uniform and fine particle size and more improved activity during a polymerization process for preparing a poly(alkylene carbonate) resin, a preparation method thereof, and a preparation method of a poly(alkylene carbonate) resin using the organic zinc catalyst.

BACKGROUND OF THE INVENTION

After the Industrial Revolution, humans established modern society while consuming huge amounts of fossil fuel, which increases a carbon dioxide concentration in the air, and the increase of the carbon dioxide concentration is further promoted by environmental destruction such as deforestation or the like. Since global warming is caused by an increase in greenhouse gases such as carbon dioxide, Freon, or methane in the air, it is important to decrease the concentration of carbon dioxide that significantly contributes to the global warming, and various researches into emission regulations, stabilization, or the like, of carbon dioxide have been conducted around the world.

Among them, a copolymerization reaction of carbon dioxide and an epoxide found by Inoue et al. has been expected to be a reaction capable of solving the global warming problem, and research has been actively conducted in view of using carbon dioxide as a carbon source as well as in view of chemical fixation of carbon dioxide. Particularly, recently, a poly(alkylene carbonate) resin formed by polymerization of carbon dioxide and an epoxide has been spotlighted as a kind of biodegradable resin.

Various catalysts for preparing this poly(alkylene carbonate) resin have been studied and suggested in the past, and as a representative catalyst, a zinc dicarboxylate-based catalyst such as a zinc glutarate catalyst in which zinc and a dicarboxylic acid are bonded to each other, or the like, has been known.

The zinc dicarboxylate-based catalyst as described above, representatively, the zinc glutarate catalyst, is formed by reacting a zinc precursor and a dicarboxylic acid such as glutaric acid, or the like, with each other, and has a fine crystalline particle shape. However, it was difficult to control the zinc dicarboxylate-based catalyst having the crystalline particle shape as described above to have a uniform and fine particle size during a preparation process. The existing zinc dicarboxylate-based catalyst has a particle size of a nanometer scale, but an aggregate having an increased particle size and a decreased surface area is formed in a medium by aggregation of catalyst particles such that at the time of preparing the poly(alkylene carbonate) resin, the activity may be deteriorated.

Therefore, there is often a case in which the existing known zinc dicarboxylate-based catalyst has a relatively large particle size and a non-uniform particle shape. Therefore, in the case of performing a polymerization process for preparing a poly(alkylene carbonate) resin using the zinc dicarboxylate-based resin, a sufficient contact area between a reactant and the catalyst is not secured, such that polymerization activity may not be sufficiently exhibited. In addition, there is often a case in which the activity of the existing zinc dicarboxylate-based catalyst itself is also not sufficient.

Further, in the case of the zinc dicarboxylate-based catalyst, it is not easy to disperse and control the catalyst particles in a reaction solution due to non-uniformity of the particle size.

SUMMARY OF THE INVENTION

The present invention has been made in an effort to provide an organic zinc catalyst having a more uniform and fine particle size and a more improved activity during a polymerization process for preparing a poly(alkylene carbonate) resin, and a preparation method thereof.

In addition, the present invention has been made in an effort to provide a preparation method of a poly(alkylene carbonate) resin using an organic zinc catalyst obtained by the preparation method.

An exemplary embodiment of the present invention provides a preparation method of an organic zinc catalyst including: reacting a zinc precursor surface-treated with a dispersant and a dicarboxylic acid having 3 to 20 carbon atoms to form a zinc dicarboxylate-based catalyst, wherein a reaction step is performed under a condition at which the number of moles of the dicarboxylic acid present in a reaction system is larger than that of the zinc precursor throughout the entire reaction step.

Another exemplary embodiment of the present invention provides an organic zinc catalyst, which is a zinc dicarboxylate-based catalyst obtained by reacting a zinc precursor surface-treated with a dispersant and a dicarboxylic acid having 3 to 20 carbon atoms, wherein 0.001 to 5 wt % of the dispersant is present on a surface of the catalyst based on a weight of the catalyst.

Another exemplary embodiment of the present invention provides a preparation method of a poly(alkylene carbonate) resin including polymerizing a monomer containing an epoxide and carbon dioxide in the presence of the organic zinc catalyst prepared by the preparation method.

Hereinafter, the preparation method of an organic zinc catalyst, an organic zinc catalyst prepared by the preparation method, and the preparation method of a poly(alkylene carbonate) resin using the organic zinc catalyst according to exemplary embodiments of the present invention will be described in detail.

Unless particularly described in the present specification, technical terms are only used to describe a specific embodiment, and are not intended to limit the present invention. In addition, singular forms used in the present specification include plural forms as long as they do not have clearly different meanings. In addition, the term 'include' used in the present specification is to specify a specific property, region, integer, step, operation, factor, and/or component, but does not exclude presence or addition of another specific property, region, integer, step, operation, factor, component, and/or group.

I. Preparation Method of Organic Zinc Catalyst

According to an exemplary embodiment of the present invention, a preparation method of an organic zinc catalyst including reacting a zinc precursor surface-treated with a dispersant and a dicarboxylic acid having 3 to 20 carbon atoms to form a zinc dicarboxylate-based catalyst is provided, wherein a reaction step is performed under a condition at which the number of moles of the dicarboxylic acid present in a reaction system is larger than that of the zinc precursor throughout the entire reaction step.

Here, "a condition at which the number of moles of the dicarboxylic acid present in a reaction system is larger than that of the zinc precursor throughout the entire reaction step" may mean that, regardless of the entire use amounts (numbers of moles) of the zinc precursor and the dicarboxylic acid required for preparation of the organic zinc catalyst, a condition that the number of moles of the dicarboxylic acid present in the reaction system (for example, a reactor) in which the reaction thereof is performed is always larger than that of the zinc precursor is maintained from a point in time at which the reaction of the zinc precursor and the dicarboxylic acid is initiated until a point in time at which the reaction is terminated.

In order to maintain this condition, a method of dividing the entire use amount of the required zinc precursor and split-injecting the zinc precursor in portions several times while injecting the entire use amount of the dicarboxylic acid at a reaction initiation point in time, or the like, may be used, and a detailed description thereof will be provided below.

Meanwhile, as a result of continuous studies of the present inventors, it was confirmed that in the case of using a zinc precursor surface-treated with a dispersant in a catalyst synthesis reaction during a process of reacting the zinc precursor and a dicarboxylic acid to prepare the zinc dicarboxylate-based catalyst, it was possible to maintain a state in which the zinc precursor was finely and uniformly dispersed in a non-polar medium as well as a polar medium, such that a zinc dicarboxylate-based catalyst having more improved activity than that of a previous catalyst may be prepared.

Further, it was confirmed that in the case of performing the reaction in a controlled state in which an excess (a molar excess) of the dicarboxylic acid was present with respect to the zinc precursor during the entire reaction process in the catalyst synthesis reaction, the zinc dicarboxylate-based catalyst having a finer and more uniform particle size and more improved activity as compared to the previous catalyst may be prepared.

The reason for this is presumed to be that, in the case of performing the reaction step in the presence of the dispersant and in an excess state of the dicarboxylic acid, zinc and the precursor or ions thereof may be uniformly dispersed in the reaction system by the dispersant, respectively, and the reaction is slowly performed in a state in which an excess of dicarboxylic acid molecules or ions enclose zinc, zinc precursor molecules, or zinc ions uniformly dispersed as described above, such that zinc corresponding to catalytically active components, or zinc precursor components are hardly aggregated with each other and may all react with a dicarboxylic acid component while being hardly aggregated with each other to form an active site of the catalyst.

In addition, it may be presumed that, due to reaction progress as described above, a risk that the zinc dicarboxylate-based catalyst particles will be aggregated with each other during the preparation process is decreased, such that finer and more uniform catalyst particles may be finally formed. Further, it may be presumed that the zinc dicarboxylate-based catalyst particles having different crystalline characteristics from catalysts according to the related art are formed due to the reaction progress as described above.

Therefore, according to an exemplary embodiment of the present invention, as a result, it was confirmed that a zinc dicarboxylate-based organic zinc catalyst having excellent activity may be obtained in a form of the catalyst particles having the finer and more uniform particle size. Further, it may be easier to disperse and control the catalyst particles in a reaction solution due to the fine and uniform particle size of the catalyst particle as described above. Therefore, the organic zinc catalyst may be preferably used to prepare a poly(alkylene carbonate) resin by the reaction of carbon dioxide and the epoxide.

In contrast, it was confirmed that, even though the entire use amount of dicarboxylic acid for preparing the organic zinc catalyst was larger than that of the zinc precursor, in the case in which the above-mentioned condition (that is, the condition at which the molar excess of the dicarboxylic acid was maintained throughout the entire reaction step) was not satisfied (for example, as in a comparative example to be described below, in the case of slowly adding the dicarboxylic acid to react with the zinc precursor, or the like, only some of the dicarboxylic acid was injected into the reaction system at at least a reaction initiation point in time, and thus the molar excess of the dicarboxylic acid may not be maintained), only a catalyst in an aggregated form may be prepared, and the activity thereof was relatively low, as compared to the organic zinc catalyst obtained in an exemplary embodiment.

Further, in the preparation method of an organic zinc catalyst, as the zinc precursor is surface-treated with the dispersant, aggregation of the zinc precursor in the medium may be minimized and the zinc precursor may have more improved dispersion stability, as compared to a zinc precursor that is not surface-treated with the dispersant. In addition, it is possible to maintain a state in which the surface-treated zinc precursor is finely, uniformly, and stably dispersed while the reaction with the dicarboxylic acid is performed.

According to an exemplary embodiment, the zinc precursor surface-treated with the dispersant may be formed by mixing the zinc precursor with the dispersant in a solvent.

Here, as the solvent, an arbitrary organic or aqueous solvent in which surface-treatment of the zinc precursor by the dispersant may be smoothly performed may be used. An example of this solvent may include one or more kinds of solvents selected from the group consisting of toluene, hexane, dimethylformamide, ethanol, and water. In the case in which a liquid medium is used in the reaction step of the zinc precursor and the dicarboxylic acid, it is preferable that the solvent used to surface-treat the zinc precursor has the same properties as those of the liquid medium.

In addition, as the zinc precursor, any zinc precursor may be used without limitation as long as it has been used to prepare the zinc dicarboxylate-based catalyst in the past, and a specific example of this zinc precursor may include zinc oxide, zinc sulfate ($ZnSO_4$), zinc chlorate ($Zn(ClO_3)_2$), zinc nitrate ($Zn(NO_3)_2$), zinc acetate ($Zn(OAc)_2$), zinc hydroxide, or the like.

Further, the dispersant, which is a component capable of uniformly dispersing the zinc precursor in the medium, may be, for example, one or more kinds of compounds selected from the group consisting of anionic surfactants, cationic surfactants, and amphiphilic surfactants. As the anionic surfactant, the cationic surfactant, and the amphiphilic surfactant, general compounds in the art to which the present invention pertains may be applied without particular limitation, respectively, and may be suitably selected in consideration of the kinds, properties, and the like, of the zinc precursor and medium used to prepare the zinc dicarboxylate-based catalyst.

Among them, in the case in which the anionic surfactant is used as the dispersant, aggregation of the zinc precursor in the medium may be further minimized, such that the anionic surfactant is advantageous. As a nonrestrictive example of the anionic surfactant, there are alkyl phenol ethoxylated phosphate esters represented by the following Chemical Formula 1.

[Chemical Formula 1]

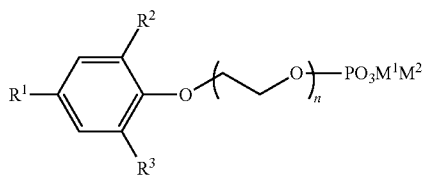

In Chemical Formula 1, $R^1$ to $R^3$ are each independently hydrogen or a straight or branched chain alkyl group having 8 to 12 carbon atoms, at least one of $R^1$ to $R^3$ being a straight or branched chain alkyl group having 8 to 12 carbon atoms;

$M^1$ and $M^2$ are each independently hydrogen, ammonium, or a monovalent metal ion; and n is an integer of 3 to 100.

As a nonrestrictive example, in Chemical Formula 1, the monovalent metal ion may be a sodium ion, a lithium ion, a potassium ion, or the like.

However, since the dispersant may be suitably selected in consideration of the kinds, properties, and the like, of the zinc precursor and medium, the dispersant is not limited to the above-mentioned examples.

In addition, the dispersant may be used at a content of 0.01 to 10 wt %, 0.1 to 10 wt %, 1 to 10 wt %, 1 to 7.5 wt %, or 1 to 5 wt %, with respect to the zinc precursor.

That is, in order to minimize aggregation of the zinc precursor and improving dispersibility, it is preferable that the dispersant is mixed at a content of 0.01 wt % or more with respect to the zinc precursor. However, in the case in which the dispersant is excessively mixed in the reaction system, the dispersant may participate in the reaction to cause a side reaction or affect a composition of the reaction medium to deteriorate a crystalline property of the catalyst, or aggregation of the zinc precursor may be induced. Therefore, it is preferable that the dispersant is used at a content of 10 wt % or less with respect to the zinc precursor.

According to an exemplary embodiment, the zinc precursor surface-treated with the dispersant as described above may have a $D_{90}$ particle size distribution of 10 μm or less, 1 to 10 μm, 1.5 to 8 μm, or 3 to 6.5 μm in the medium for the reaction with the dicarboxylic acid.

Here, $D_{90}$, which represents a particle size at which an accumulated volume is 90% of the total volume of particles when particles are accumulated from particles having a small particle size, means a size of the aggregate formed by aggregation of the precursor in a state in which the zinc precursor is mixed in the medium.

As the zinc precursor is surface-treated with the dispersant, particle size distribution may be stably maintained during the reaction with the dicarboxylic acid.

However, in the case of using a zinc precursor having a $D_{90}$ particle size distribution of larger than 10 μm (that is, in the case in which a secondary particle of larger than 10 μm is formed in the medium by aggregation of the zinc precursor) in the reaction with the dicarboxylic acid, it is difficult to uniformly perform the reaction with the dicarboxylic acid, the zinc precursor is precipitated before the reaction is completed, and so on, such that a stable dispersion state may not be maintained.

Meanwhile, as the dicarboxylic acid reacting with the zinc precursor as described above, an arbitrary dicarboxylic acid having 3 to 20 carbon atoms may be used. More specifically, an aliphatic dicarboxylic acid selected from the group consisting of malonic acid, glutaric acid, succinic acid, and adipic acid, or an aromatic dicarboxylic acid selected from the group consisting of terephthalic acid, isophthalic acid, homophthalic acid, and phenyl glutaric acid, may be used.

Otherwise, various aliphatic or aromatic dicarboxylic acids having 3 to 20 carbon atoms may be used. However, in view of the activity of the organic zinc catalyst, or the like, it is preferable that the dicarboxylic acid is glutaric acid, and that the zinc dicarboxylate-based organic zinc catalyst is a zinc glutarate-based catalyst.

Meanwhile, in the preparation method according to an exemplary embodiment, several means may be applied so that the condition in which the molar excess of the dicarboxylic acid is present in the reaction system may be maintained throughout the entire reaction step.

As a first means, in view of the entire use amount, the dicarboxylic acid is used in a sufficient molar excess as compared to the zinc precursor, and the entire use amount of the dicarboxylic acid is injected at the reaction initiation point in time, such that a molar excess condition of the dicarboxylic acid may be maintained through the entire reaction step.

More specifically, the dicarboxylic acid may be used at a ratio of about 1.05 to 1.5 moles or 1.1 to 1.3 moles based on 1 mole of the zinc precursor, and this entire use amount of the dicarboxylic acid may be injected at the reaction initiation point in time. As the reaction is performed while maintaining the molar excess state of the dicarboxylic acid by controlling the entire use amount as described above, the organic zinc catalyst in a form of the zinc dicarboxylate-based catalyst having a more uniform and fine particle size and improved activity may be prepared.

Further, as a second means, the reaction step is performed in a liquid medium in which reactants including the zinc precursor and the dicarboxylic acid are present (for example, the reaction is performed in a state of a solution or dispersion in which the reactants are dissolved or dispersed), but the reaction may be performed while adding a solution or dispersion containing the zinc precursor in portions two times or more that of a solution or dispersion containing the dicarboxylic acid.

That is, the entire reaction step may be performed in the molar excess state of the dicarboxylic acid in the reaction system by primarily injecting some of the solution or dispersion containing the zinc precursor to perform the reaction, and performing the rest of the reaction while adding the rest of the solution or dispersion containing the zinc precursor in portions. Therefore, the organic zinc catalyst in a form of the zinc dicarboxylate-based catalyst having a more uniform and fine particle size and improved activity may be obtained.

In this case, a method of adding the solution or dispersion containing the zinc precursor in portions 2 times or more is not particularly limited, and several methods may be used.

First, as an example, after obtaining solutions or dispersions containing the zinc precursor at amounts obtained by dividing the entire use amount of the zinc precursor into 2 to 10, respectively, these solutions or dispersions may be added in portions 2 to 10 times to the solution or dispersion containing the dicarboxylic acid at the same time interval while performing the reaction. In this case, properly, after obtaining each of the solutions or dispersions containing the zinc precursor at amounts obtained by dividing the entire use amount of the zinc precursor into 2 to 5, respectively, these solution or dispersions may be added in portions 2 to 5 times.

Therefore, the organic zinc catalyst having the more improved activity, or the like, may be prepared by effectively maintaining the mole excess condition of the dicarboxylic acid in the reaction system while further increasing productivity of the preparation process of the catalyst.

As another example, the entire reaction step may be performed while uniformly dripping the solution or dispersion containing the zinc precursor in a droplet form into the solution or dispersion containing the dicarboxylic acid.

Meanwhile, the condition in which the molar excess state of the dicarboxylic acid is maintained throughout the entire reaction step may be appropriately achieved by applying the first means (entire use amount control) and the second means (split-injection of the zinc precursor) together with each other.

In addition, when the reaction step of the zinc precursor and the dicarboxylic acid is performed in the liquid medium, as the liquid medium, any organic or aqueous solvent known to uniformly dissolve or disperse the zinc precursor and/or the dicarboxylic acid may be used. A specific example of the liquid medium as described above may include one or more kinds of solvents selected from the group consisting of toluene, hexane, dimethylformamide, ethanol, and water.

Further, the reaction step of the zinc precursor and the dicarboxylic acid may be performed at about 50 to 130° C. for about 1 to 10 hours. In addition, as the zinc precursor is added in portions at the same time interval in the entire reaction time, the molar excess state of the dicarboxylic acid in the reaction system may be maintained throughout the entire reaction step as described above. The zinc dicarboxylate-based organic zinc catalyst having a finer and more uniform particle size and improved physical properties may be prepared with a high yield by performing the reaction step under the reaction condition as described above.

A catalyst prepared by the existing method has a particle size of about 1 to 2 μm, but as the preparation method of an organic zinc catalyst is optimized as described above, the organic zinc catalyst obtained by the above-mentioned method may be in a form of uniform particles having an average particle size of about 0.8 μm or less or about 0.5 to 0.7 μm, and a particle size standard deviation of about 0.2 μm or less or about 0.05 to 1 μm.

As described above, as the organic zinc catalyst has a finer and more uniform particle size, the organic zinc catalyst may have a surface area of about 1.8 $m^2/g$ or more, or about 1.8 to 2.5 $m^2/g$, or larger than about 1.1 to 1.3 $m^2/g$, which is a surface area of the existing catalyst. Therefore, when the organic zinc catalyst is used as a catalyst at the time of preparing a poly(alkylene carbonate) resin by copolymerization of carbon dioxide and the epoxide, contact areas between the catalyst particle and reactants may be further increased, such that the activity may be improved.

II. Organic Zinc Catalyst

Meanwhile, according to another exemplary embodiment of the present invention, an organic zinc catalyst, which is a zinc dicarboxylate-based catalyst obtained by reacting a zinc precursor surface-treated by a dispersant and a dicarboxylic acid having 3 to 20 carbon atoms is provided, wherein 0.001 to 5 wt % of the dispersant is present on a surface of the catalyst based on a weight of the catalyst.

Preferably, the organic zinc catalyst, which is obtained by reacting the zinc precursor surface-treated with the dispersant and dicarboxylic acid, may be prepared by the above-mentioned method.

That is, as described above, the organic zinc catalyst is prepared in a state in which the zinc precursor is optimally dispersed, such that the organic zinc catalyst may be in a form of uniform particles having an average particle size of about 0.8 μm or less or about 0.5 to 0.7 μm, as compared to an organic zinc catalyst prepared by the existing method (for example, a general organic zinc catalyst having a primary particle size of about 1 to 2 μm).

Here, the 'primary particle size' of the catalyst means a size of a catalyst particle itself in a state in which the catalyst is not mixed with a medium, and a 'secondary particle size' of the catalyst relatively means a size of an aggregate formed by aggregation of the catalyst particles in a state in which the catalyst is mixed with the medium. The primary particle size may be confirmed using an electron microscope or the like.

In addition, as the organic zinc catalyst has a finer and more uniform particle size, the organic zinc catalyst may have a surface area that is increased by about 1.5 to 6 times compared to a surface area of the existing catalyst (for example, about 1.1 to 1.3 $m^2/g$).

Further, the dispersant used to surface-treat the zinc precursor may contribute to improving dispersibility of the finally produced organic zinc catalyst as well as dispersibility of the zinc precursor. That is, the zinc precursor surface-treated with the dispersant reacts with the dicarboxylic acid to form a zinc carboxylate particle, and the dispersant separated during this process stabilizes the zinc carboxylate particle, thereby improving the dispersibility. Therefore, at the time of measuring the particle size (secondary particle size) of the organic zinc catalyst in the presence of an ethanol solvent, the organic zinc catalyst may have a $D_{50}$ particle size distribution of 5 μm or less, 1 to 5 μm, 1 to 3 μm, or 1 to 5.5 μm.

Further, according to an exemplary embodiment, a synthesized organic zinc catalyst may be subjected to a washing process and a drying process, and even though the organic zinc catalyst is subjected to the washing process, a predetermined amount of the dispersant may remain in the surface of the catalyst. In this case, a content of the dispersant present in the surface of the catalyst may be 5 wt % or less, 0.001 to 5 wt %, 0.001 to 3 wt %, or 0.01 to 1.5 wt % based on a weight of the catalyst.

That is, in the case in which the dispersant is excessively present in the surface of the catalyst, the dispersant may block an active surface of the catalyst at the time of preparing a poly(alkylene carbonate) resin using the catalyst to decrease the activity of the catalyst, and a molecular weight of a final resin may be decreased or side reactions may be increased, etc., such that reaction efficiency may be decreased. Therefore, it is preferable that the content of the dispersant present in the surface of the catalyst is 5 wt % or less based on the weight of the catalyst.

In relation to this, in the past, it is known that in order to improve dispersibility of a general organic zinc catalyst at the time of preparing a poly(alkylene carbonate) resin, a dispersant should be used at a degree in which a dispersant layer having a thickness of 10 nm or more may be formed on a surface of the organic zinc catalyst. For example, theoretically, in order to form a dispersant layer having a thickness of 10 nm on a surface of a zinc glutarate catalyst (density: about 2.1 g/cm$^3$) having a surface area of 10 to 20 m$^2$/g, 10 to 25 wt % of the dispersant should be used based on a weight of the catalyst. In this case, a density of the dispersant layer is assumed as about 1 g/cm$^3$.

On the contrary, as the organic zinc catalyst provided in the present invention is prepared by the above-mentioned method, the catalyst has a further increased surface area compared to that of a previous catalyst, and stable dispersibility of the catalyst may be secured even with 5 wt % or less of the dispersant based on the weight of the catalyst. This amount is a significantly smaller amount than an amount of the theoretically required dispersant (10 to 25 wt % based on the weight of the catalyst), and corresponds to a significantly small amount in consideration of the increased surface area.

Therefore, when the organic zinc catalyst is used as a catalyst at the time of preparing a poly(alkylene carbonate) resin by copolymerization of carbon dioxide and an epoxide, contact areas between the catalyst particle and reactants may be further increased, such that the activity may be improved.

III. Preparation Method of Poly(Alkylene Carbonate) Resin Using the Catalyst

According to another exemplary embodiment of the present invention, a preparation method of a poly(alkylene carbonate) resin is provided, including polymerizing a monomer containing an epoxide and carbon dioxide in the presence of the organic zinc catalyst prepared by the preparation method according to an exemplary embodiment of the present invention.

In the preparation method of a resin as described above, the organic zinc catalyst may be used in a form of a non-uniform catalyst, and the polymerizing may be performed by solution polymerization in an organic solvent. Therefore, reaction heat may be suitably controlled, and it may be easy to control a molecular weight or viscosity of a desired poly(alkylene carbonate) resin.

In this solution polymerization, as the solvent, one or more kinds selected from the group consisting of methylene chloride, ethylene dichloride, trichloroethane, tetrachloroethane, chloroform, acetonitrile, propionitrile, dimethylformamide, N-methyl-2-pyrrolidone, dimethyl sulfoxide, nitromethane, 1,4-dioxane, hexane, toluene, tetrahydrofuran, methylethylketone, methylamineketone, methyl isobutyl ketone, acetone, cyclohexanone, trichloroethylene, methyl acetate, vinyl acetate, ethyl acetate, propyl acetate, butyrolactone, caprolactone, nitropropane, benzene, styrene, xylene, and methyl propasol may be used. Among them, when methylene chloride or ethylene dichloride is used as the solvent, a polymerization reaction may be more effectively performed.

The solvent may be used in a weight ratio of about 1:0.5 to 1:100, preferably about 1:1 to 1:10 based on the epoxide. Here, in the case in which the ratio is excessively low (less than about 1:0.5), the solvent does not suitably serve as a reaction medium, such that it may be difficult to implement advantages of the solution polymerization as described above. Further, in the case in which the ratio is more than about 1:100, a concentration of the epoxide or the like is relatively decreased, such that productivity may be deteriorated, a molecular weight of a finally formed resin may be decreased, or side reactions may be increased.

In addition, the organic zinc catalyst may be injected in a molar ratio of about 1:50 to 1:1000 based on the epoxide. More preferably, the organic zinc catalyst may be injected in a molar ratio of about 1:70 to 1:600, or 1:80 to 1:300, based on the epoxide. In the case in which the ratio is excessively small, it is difficult to obtain sufficient catalytic activity at the time of solution polymerization. On the contrary, in the case in which the ratio is excessively large, an excessive amount of catalyst is used, which is not efficient, and by-products may be formed, or back-biting of the resin may occur due to heating in the presence of the catalyst.

Meanwhile, as the epoxide, one or more kinds selected from the group consisting of alkylene oxides having 2 to 20 carbon atoms, substituted or unsubstituted with a halogen or an alkyl group having 1 to 5 carbon atoms; cyclo alkylene oxides having 4 to 20 carbon atoms substituted or unsubstituted with a halogen or an alkyl group having 1 to 5 carbon atoms; and styrene oxides having 8 to 20 carbon atoms substituted or unsubstituted with a halogen or an alkyl group having 1 to 5 carbon atoms may be used. As a representative epoxide, an alkylene oxide having 2 to 20 carbon atoms, substituted or unsubstituted with a halogen or an alkyl group having 1 to 5 carbon atoms, may be used.

Specific examples of the epoxide as described above may include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxy-7-octene, epifluorohydrin, epichlorohydrin, epibromohydrin, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxynorbornene, limonene oxide, dieldrin, 2,3-epoxypropylbenzene, styrene oxide, phenylpropylene oxide, stilbene oxide, chlorostilbene oxide, dichlorostilbene oxide, 1,2-epoxy-3-phenoxypropane, benzyloxymethyl oxirane, glycidyl-methylphenyl ether, chlorophenyl-2,3-epoxypropyl ether, epoxypropyl methoxyphenyl ether, biphenyl glycidyl ether, glycidyl naphthyl ether, and the like. As the most representative epoxide, ethylene oxide is used.

In addition, the above-mentioned solution polymerization may be performed at about 50 to 100° C. and at about 15 to 50 bar for about 1 to 60 hours. Further, the above-mentioned solution polymerization may be more preferably performed at about 70 to 90° C. and at about 20 to 40 bar for about 3 to 40 hours.

Meanwhile, since other polymerization processes and conditions except for the above-mentioned contents may depend on general polymerization conditions for preparing a poly(alkylene carbonate) resin, and the like, a detailed description thereof will be omitted.

According to the present invention, the preparation process of the catalyst is optimized, such that the organic zinc catalyst for preparing a poly(alkylene carbonate) resin, having a finer and more uniform particle size and excellent activity, may be prepared and provided.

DETAILED DESCRIPTION OF THE PREFERRED EMBODIMENTS

Hereinafter, preferred examples of the present invention will be provided for understanding of the present invention. It is to be understood that the examples are only for illustrative purposes and are not intended to limit the scope of the present invention.

EXAMPLE 1: Preparation of Organic Zinc Catalyst in Presence of Dispersant (Molar Ratio of ZnO and Glutaric Acid=1:1.2)

In a 250 mL round bottom flask, 7.93 g (0.06 mol) of glutaric acid and 0.1 mL of acetic acid were added to and dispersed in 100 mL of toluene under reflux, followed by heating at 55° C. for 30 minutes.

Separately, 4.1 g (0.05 mol) of ZnO was added to and stirred with 50 mL of toluene to which 0.02 g of nonylphenol ethoxylated phosphate ester was added, thereby preparing a Zn dispersion.

The ZnO dispersion was divided into 4 portions based on volume, and a reaction was performed by primarily adding a ¼ portion of the ZnO dispersion to a glutaric acid solution. After 1 hour, the reaction was performed by adding another ¼ portion of the ZnO dispersion, and after 1 hour therefrom, the reaction was performed by adding another ¼ portion of the ZnO dispersion. After another hour, the reaction was performed by adding the remaining ¼ portion of the ZnO dispersion. The mixed solution was heated at 110° C. for 2 hours. After a white solid was produced, the produced white solid was filtered, washed with acetone/ethanol, and dried at 130° C. in a vacuum oven.

An organic zinc catalyst of Example 1 was prepared by the method as described above. As a result of scanning electron microscope (SEM) analysis, it was confirmed that the organic zinc catalyst of Example 1 had an average particle size of about 0.2 μm and a particle size standard deviation of 0.04 μm.

EXAMPLE 2: Preparation of Organic Zinc Catalyst in Presence of Dispersant (Molar Ratio of ZnO and Glutaric Acid=1:1.5)

In a 250 mL round bottom flask, 9.91 g (0.075 mol) of glutaric acid and 0.1 mL of acetic acid were added to and dispersed in 100 mL of toluene under reflux, followed by heating at 55° C. for 30 minutes.

Separately, 4.1 g (0.05 mol) of ZnO was added to and stirred with 50 mL of toluene to which 0.02 g of nonylphenol ethoxylated phosphate ester was added, thereby preparing a Zn dispersion.

The ZnO dispersion was divided into 4 portions based on volume, and a reaction was performed by adding a ¼ portion of the ZnO dispersion to a glutaric acid solution. After 1 hour, the reaction was performed by adding another ¼ portion of the ZnO dispersion, and after 1 hour therefrom, the reaction was performed by adding another ¼ portion of the ZnO dispersion. After an additional hour, the reaction was performed by adding the remaining ¼ portion of the ZnO dispersion. The mixed solution was heated at 110° C. for 2 hours. After a white solid was produced, the produced white solid was filtered, washed with acetone/ethanol, and dried at 130° C. in a vacuum oven.

An organic zinc catalyst of Example 2 was prepared by the method as described above. As a result of scanning electron microscope (SEM) analysis, it was confirmed that the organic zinc catalyst of Example 2 had an average particle size of about 0.25 μm and a particle size standard deviation of 0.03 μm.

EXAMPLE 3: Preparation of Organic Zinc Catalyst in Presence of Dispersant (Molar Ratio of ZnO and Glutaric Acid=1:1)

In a 250 mL round bottom flask, 6.61 g (0.05 mol) of glutaric acid and 0.1 mL of acetic acid were added to and dispersed in 100 mL of toluene under reflux, followed by heating at 55° C. for 30 minutes.

Separately, 4.1 g (0.05 mol) of ZnO was added to and stirred with 50 mL of toluene to which 0.02 g of nonylphenol ethoxylated phosphate ester was added, thereby preparing a Zn dispersion.

The ZnO dispersion was divided into 4 portions based on volume, and a reaction was performed by adding a ¼ portion of the ZnO dispersion to a glutaric acid solution. After 1 hour, the reaction was performed by adding another ¼ portion of the ZnO dispersion, and after 1 hour therefrom, the reaction was performed by adding another ¼ portion of the ZnO dispersion. After an additional hour, the reaction was performed by adding the remaining ¼ portion of the ZnO dispersion. The mixed solution was heated at 110° C. for 2 hours. After a white solid was produced, the produced white solid was filtered, washed with acetone/ethanol, and dried at 130° C. in a vacuum oven.

An organic zinc catalyst of Example 3 was prepared by the method as described above. As a result of scanning electron microscope (SEM) analysis, it was confirmed that the organic zinc catalyst of Example 3 had an average particle size of about 0.6 μm and a particle size standard deviation of 0.18 μm.

EXAMPLE 4: Preparation of Organic Zinc Catalyst in Presence of Dispersant Molar Ratio of Zinc Nitrate [$Zn(NO_3)_2$] and Glutaric Acid=1:1.2

An organic zinc catalyst of Example 4 was prepared by the same method as in Example 1, except for using 11.36 g (0.06 mol) of $Zn(NO_3)_2$ instead of ZnO as a zinc precursor.

The organic zinc catalyst of Example 4 was confirmed by SEM analysis, and as a result, it was confirmed that that the organic zinc catalyst of Example 4 had an average particle size of about 0.8 μm and a particle size standard deviation of about 0.20 μm.

COMPARATIVE EXAMPLE 1: Preparation of Organic Zinc Catalyst (Molar Ratio of ZnO and Glutaric Acid=1:1)

In a 250 mL round bottom flask, 6.61 g (0.05 mol) of glutaric acid, 4.1 g (0.05 mol) of ZnO, and 0.1 mL of acetic acid were added to and dispersed in 150 mL of toluene under reflux. Then, the mixed solution was heated at 55° C. for 3 hours and at 110° C. for 4 hours. After a white solid was produced, the produced white solid was filtered, washed with acetone/ethanol, and dried at 130° C. in a vacuum oven.

An organic zinc catalyst of Comparative Example 1 was prepared by the method as described above. As a result of scanning electron microscope (SEM) analysis, it was confirmed that the organic zinc catalyst of Comparative Example 1 had a particle size of about 1 to 2 μm and a particle size standard deviation of 0.4 μm or more.

COMPARATIVE EXAMPLE 2: Preparation of Organic Zinc Catalyst (Molar Ratio of ZnO and Glutaric Acid=1:1.2)

In a 250 mL round bottom flask, 7.93 g (0.06 mol) of glutaric acid and 0.1 mL of acetic acid were added to and dispersed in 100 mL of toluene under reflux, followed by heating at 55° C. for 30 minutes.

Separately, 4.1 g (0.05 mol) of ZnO was added to and stirred with 50 mL of toluene, thereby preparing a ZnO dispersion.

The glutaric acid dispersion was divided into 4 portions based on volume, and a reaction was performed by adding a ¼ portion of glutaric acid dispersion to the ZnO solution. After 1 hour, the reaction was performed by adding another ¼ portion of the glutaric acid dispersion, and after 1 hour therefrom, the reaction was performed by adding another ¼ portion of the glutaric acid dispersion. After an additional hour, the reaction was performed by adding the remaining ¼ portion of the glutaric acid dispersion. The mixed solution was heated at 110° C. for 2 hours. After a white solid was produced, the produced white solid was filtered, washed with acetone/ethanol, and dried at 130° C. in a vacuum oven.

An organic zinc catalyst of Comparative Example 2 was prepared by the method as described above. The organic zinc catalyst of Comparative Example 2 was confirmed by SEM analysis, and as a result, it was confirmed that that the organic zinc catalyst of Example 2 had an average particle size of about 1.7 μm and a particle size standard deviation of about 0.43 μm or more.

Polymerization Example

Polyethylene carbonate was polymerized and prepared by the following method using the catalysts of the examples and comparative examples.

First, in a glove box, 0.4 g of the catalyst and 8.25 g of dichloromethane (methylene chloride) were put into a high pressure reactor, and 8.9 g of ethylene oxide was added thereto. Thereafter, the reactor was pressurized to 30 bar using carbon dioxide. A polymerization reaction was performed at 70° C. for 3 hours. After the reaction was terminated, unreacted carbon dioxide and ethylene oxide were removed together with dichloromethane, which was a solvent. In order to confirm an amount of the prepared polyethylene carbonate, the remaining solid was completely dried and then weighed. Activities and yields of the catalysts depending on results of the polymerization as described above are shown in the following Table 1.

TABLE 1

| | Molar ratio of ZnO:Glutaric acid | Yield (g) | Activity of catalyst (g-polymer/g-catalyst) |
|---|---|---|---|
| Example 1 | 1:1.2 | 20.9 | 67.0 |
| Example 2 | 1:1.5 | 16.5 | 64.2 |
| Example 3 | 1:1 | 20.1 | 50.3 |
| Example 4[a] | 1:1.2 | 14.3 | 35.8 |
| Comparative Example 1[b] | 1:1 | 11.9 | 29.8 |
| Comparative Example 2[c] | 1:1.2 | 10.2 | 25.5 |

[a] Zn(NO₃)₂ was used instead of ZnO
[b] ZnO and glutaric acid were injected at once
[c] Glutaric acid was injected in portions to the ZnO dispersion Referring to Table 1, it was confirmed that the catalysts of the examples had excellent activities as compared to the catalysts of the comparative examples, and preparation of polyethylene carbonate with high yields was enabled.

What is claimed is:

1. A preparation method of an organic zinc catalyst, the preparation method comprising:
   providing a zinc precursor surface-treated with a dispersant; and
   reacting the surface-treated zinc precursor with a dicarboxylic acid having 3 to 20 carbon atoms to form a zinc dicarboxylate-based catalyst,
   wherein the reaction step is performed under a condition at which the number of moles of the dicarboxylic acid present in a reaction system is larger than that of the zinc precursor throughout the entire reaction step,
   wherein the dispersant is an anionic surfactant.

2. The preparation method of claim 1, wherein the dispersant is an alkyl phenol ethoxylated phosphate ester represented by the following Chemical Formula 1:

[Chemical Formula 1]

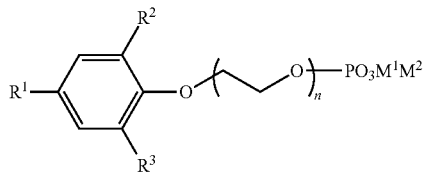

wherein, in Chemical Formula 1,
$R^1$ to $R^3$ are each independently hydrogen or a straight or branched chain alkyl group having 8 to 12 carbon atoms, at least one of $R^1$ to $R^3$ being a straight or branched chain alkyl group having 8 to 12 carbon atoms;
$M^1$ and $M^2$ are each independently hydrogen, ammonium, or a monovalent metal ion; and
n is an integer of 3 to 100.

3. The preparation method of claim 1, wherein the zinc precursor surface treated by the dispersant is formed by mixing the zinc precursor with the dispersant in a solvent.

4. The preparation method of claim 3, wherein the dispersant is mixed at a content of 0.01 to 10 wt % with respect to the zinc precursor.

5. The preparation method of claim 1, wherein the dicarboxylic acid is used in a ratio of 1.05 to 1.5 moles based on 1 mole of the zinc precursor.

6. The preparation method of claim 1, wherein the zinc precursor includes a zinc compound selected from the group consisting of zinc oxide, zinc sulfate ($ZnSO_4$), zinc chlorate ($Zn(ClO_3)_2$), zinc nitrate ($Zn(NO_3)_2$), zinc acetate ($Zn(OAc)_2$), and zinc hydroxide.

7. The preparation method of claim 1, wherein the dicarboxylic acid having 3 to 20 carbon atoms includes an aliphatic dicarboxylic acid selected from the group consisting of malonic acid, glutaric acid, succinic acid, and adipic acid, or an aromatic dicarboxylic acid selected from the group consisting of terephthalic acid, isophthalic acid, homophthalic acid, and phenyl glutaric acid.

8. The preparation method of claim 1, wherein the reaction step is performed in a liquid medium,
   while adding a solution or dispersion containing the zinc precursor in portions 2 times or more to a solution or dispersion containing the dicarboxylic acid.

9. The preparation method of claim 8, wherein the reaction step is performed while adding a solution or dispersion containing the zinc precursor at an amount obtained by dividing the entire use amount of the zinc precursor into 2 to 10 to the solution or dispersion containing the dicarboxylic acid at the same time interval.

10. The preparation method of claim 8, wherein the reaction step is performed while dripping the solution or dispersion containing the zinc precursor in a droplet form into the solution or dispersion containing the dicarboxylic acid.

11. The preparation method of claim 8, wherein the liquid medium includes one or more kinds of solvents selected from the group consisting of toluene, hexane, dimethylformamide, ethanol, and water.

12. The preparation method of claim 1, wherein the organic zinc catalyst is in a form of particles having an average particle size of 0.5 μm or less.

13. The preparation method of claim 1, wherein the organic zinc catalyst having a surface area of 1.8 m²/g or more is prepared.

* * * * *